(12) United States Patent
Tankiewicz et al.

(10) Patent No.: US 12,310,693 B2
(45) Date of Patent: *May 27, 2025

(54) ANALYTE SENSOR TRANSCEIVER CONFIGURED TO PROVIDE TACTILE, VISUAL, AND/OR AURAL FEEDBACK

(71) Applicant: Senseonics, Incorporated, Germantown, MD (US)

(72) Inventors: Szymon Tankiewicz, Germantown, MD (US); Jeremy Emken, Germantown, MD (US); Andrew DeHennis, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 940 days.

This patent is subject to a terminal disclaimer.

(21) Appl. No.: 17/462,640

(22) Filed: Aug. 31, 2021

(65) Prior Publication Data

US 2021/0393127 A1    Dec. 23, 2021

Related U.S. Application Data

(60) Continuation of application No. 16/173,502, filed on Oct. 29, 2018, now Pat. No. 11,116,399, which is a
(Continued)

(51) Int. Cl.
*A61B 5/1455* (2006.01)
*A61B 5/00* (2006.01)
(Continued)

(52) U.S. Cl.
CPC .............. *A61B 5/0002* (2013.01); *A61B 5/01* (2013.01); *A61B 5/1112* (2013.01);
(Continued)

(58) Field of Classification Search
None
See application file for complete search history.

(56) References Cited

U.S. PATENT DOCUMENTS 5,846,188 A   12/1998  Palti
6,304,766 B1  10/2001  Colvin, Jr.
(Continued)

FOREIGN PATENT DOCUMENTS

JP    2008-206575 A    9/2008
JP    2010-500078 A    1/2010
(Continued)

*Primary Examiner* — Marjan Fardanesh
(74) *Attorney, Agent, or Firm* — Rothwell, Figg, Ernst & Manbeck, P.C.

(57) ABSTRACT

A transceiver for interfacing with an analyte sensor. The transceiver may include an interface device and a notification device. The interface device may be configured to convey a power signal to the analyte sensor and to receive data signals from the analyte sensor. The notification device may be configured to generate one or more of a vibrational, aural, and visual signal based on one or more data signals received from the analyte sensor. The interface device of the transceiver may receive analyte data from the analyte sensor, and the transceiver may comprise a processor configured to calculate an analyte concentration value based on the received analyte data. The notification device may be configured to generate one or more of aural, visual, or vibrational alarm when the calculated analyte concentration value exceeds or falls below a threshold value.

24 Claims, 3 Drawing Sheets

Related U.S. Application Data division of application No. 14/453,078, filed on Aug. 6, 2014, now Pat. No. 10,111,588, which is a continuation-in-part of application No. 13/937,871, filed on Jul. 9, 2013, now Pat. No. 9,414,775, and a continuation-in-part of application No. 13/853,095, filed on Mar. 29, 2013, now Pat. No. 9,345,426.

(60) Provisional application No. 61/881,679, filed on Sep. 24, 2013, provisional application No. 61/865,373, filed on Aug. 13, 2013, provisional application No. 61/864,174, filed on Aug. 9, 2013, provisional application No. 61/617,414, filed on Mar. 29, 2012.

(51) Int. Cl.
*A61B 5/01* (2006.01)
*A61B 5/11* (2006.01)
*A61B 5/145* (2006.01)
*A61B 5/1459* (2006.01)

(52) U.S. Cl.
CPC ........ *A61B 5/14532* (2013.01); *A61B 5/1459* (2013.01); *A61B 5/7282* (2013.01); *A61B 5/7405* (2013.01); *A61B 5/742* (2013.01); *A61B 5/7455* (2013.01); *A61B 5/14503* (2013.01); *A61B 5/7203* (2013.01)

(56) References Cited

U.S. PATENT DOCUMENTS

| | | |
|---|---|---|
| 6,422,066 B1 | 7/2002 | Cordonnier et al. |
| 6,790,178 B1 | 9/2004 | Mault et al. |
| 2002/0019586 A1 | 2/2002 | Teller et al. |
| 2002/0128546 A1 | 9/2002 | Silver |
| 2002/0151772 A1 | 10/2002 | Polak |
| 2003/0208113 A1 | 11/2003 | Mault et al. |
| 2004/0186390 A1 | 9/2004 | Ross et al. |
| 2005/0236580 A1 | 10/2005 | Colvin, Jr. et al. |
| 2007/0014726 A1 | 1/2007 | Merical et al. |
| 2007/0163880 A1 | 7/2007 | Woo et al. |
| 2008/0108885 A1 | 5/2008 | Colvin, Jr. |
| 2008/0208480 A1 | 8/2008 | Kuriyama et al. |
| 2009/0240120 A1 | 9/2009 | Mensinger et al. |
| 2009/0312621 A1 | 12/2009 | Verbitskiy et al. |
| 2010/0024526 A1 | 2/2010 | Colvin, Jr. |
| 2011/0050428 A1 | 3/2011 | Istoc |
| 2011/0193704 A1 | 8/2011 | Harper et al. |
| 2012/0029327 A1 | 2/2012 | Angelides |
| 2012/0053427 A1 | 3/2012 | Markle et al. |
| 2012/0130203 A1 | 5/2012 | Stergiou et al. |
| 2012/0223251 A1 | 9/2012 | Morrow et al. |
| 2012/0245444 A1 | 9/2012 | Otis et al. |
| 2013/0120147 A1 | 5/2013 | Narasimhan et al. |
| 2013/0211213 A1 | 8/2013 | DeHennis et al. |
| 2013/0241745 A1 | 9/2013 | Colvin, Jr. et al. |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0018644 A1 | 1/2014 | Colvin, Jr. et al. |
| 2014/0350359 A1 | 11/2014 | Tankiewicz et al. |
| 2015/0141770 A1 | 5/2015 | Rastogi et al. |
| 2015/0157263 A1 | 6/2015 | Workman et al. |
| 2017/0215815 A1 | 8/2017 | Rastogi et al. |
| 2019/0059727 A1 | 2/2019 | Tankiewicz et al. |
| 2019/0076022 A1 | 3/2019 | Tankiewicz et al. |

FOREIGN PATENT DOCUMENTS

| | | |
|---|---|---|
| WO | 2010/022387 A1 | 2/2010 |
| WO | 2010/141888 A1 | 12/2010 |
| WO | 2011/003035 A1 | 1/2011 |
| WO | 2011/091336 A1 | 7/2011 |
| WO | 2012/123765 A1 | 9/2012 |
| WO | 2013/055962 A1 | 4/2013 |
| WO | 2013/086564 A1 | 6/2013 |
| WO | 2013/090731 A1 | 6/2013 |
| WO | 2013/149129 A1 | 10/2013 |
| WO | 2015/103022 A1 | 7/2015 |

ANALYTE SENSOR TRANSCEIVER CONFIGURED TO PROVIDE TACTILE, VISUAL, AND/OR AURAL FEEDBACK

CROSS-REFERENCE TO RELATED APPLICATIONS

The present application is a continuation of U.S. patent application Ser. No. 16/173,502, filed on Oct. 29, 2018, which is a divisional of U.S. patent application Ser. No. 14/453,078, filed on Aug. 6, 2014, now U.S. Pat. No. 10,111,588, which (a) claims the benefit of priority to U.S. Provisional Application Ser. No. 61/864,174, filed on Aug. 9, 2013; U.S. Provisional Application Ser. No. 61/865,373, filed on Aug. 13, 2013; and U.S. Provisional Application Ser. No. 61/881,679, filed on Sep. 24, 2013; and (b) is a continuation-in-part of U.S. patent application Ser. No. 13/937,871, which was filed on Jul. 9, 2013, now U.S. Pat. No. 9,414,775, and is a continuation-in-part of U.S. patent application Ser. No. 13/853,095, which was filed on Mar. 29, 2013, now U.S. Pat. No. 9,345,426, and claims the benefit of priority to U.S. Provisional Application Ser. No. 61/617,414, filed on Mar. 29, 2012, all of which are incorporated by reference in their entireties.

FIELD OF THE INVENTION

The invention is directed to an on-body, wearable transceiver for communication with an analyte sensor, where the sensor is implanted subcutaneously, intravenously, or intraperitoneally. The transceiver may provide visual, vibratory/tactile, and/or aural notifications/feedback to the user. The transceiver may also provide wireless communication to and exchange data with a smartphone or other device, which may also have visual, vibratory/tactile, and/or aural notifications/feedback.

BACKGROUND OF INVENTION

Conventional continuous analyte (e.g., glucose) monitoring systems include a sensor, a transceiver worn on the user and configured for communication with the sensor, and a receiver, separate from the transceiver and configured to receive data transmissions from the transceiver and to provide notifications and feedback to the user. In conventional systems, all alarms and/or other aural, visual or vibratory notifications are provided by the receiver. The receiver shows the user both passive and actionable information and provides visual/aural/vibratory alarms. In some systems, the transceiver is also connected (either by wire or wirelessly) to either to an insulin pump or a personal communication device, such as a smartphone, in which case the visual and/or aural and/or vibratory alarm/notification systems are incorporated into either the insulin pump or the communication device.

A disadvantage of conventional analyte monitoring systems is that in order for a user to receive any visual, aural or vibratory alarms and/or information related to the analyte measurements, the user is required to be within close proximity of the receiver in order to see, hear, or feel the alarm. Thus, improvements in analyte monitoring systems are desired.

SUMMARY OF THE INVENTION

An analyte monitoring system embodying aspects of the present invention may comprise an analyte sensor and an externally-worn transceiver configured for communication with the sensor which includes the capabilities of having the transceiver vibrate and/or generate an aural or visual signal to prompt the user about sensor and/or transceiver information, in addition to having these capabilities reside on the smartphone application.

One aspect of the present invention may provide a transceiver for interfacing with an analyte sensor. The transceiver may include an interface device and a notification device. The interface device may be configured to convey a power signal to the analyte sensor and to receive data signals from the analyte sensor. The notification device may be configured to generate one or more of a vibrational, aural, and visual signal based on one or more data signals received from the analyte sensor.

In some embodiments, the interface device may be an antenna configured to wirelessly convey the power signal to an antenna of the analyte sensor and to wirelessly receive the data signals from the antenna of the analyte sensor. In some embodiments, the notification device may be configured to generate one or more of a vibrational, aural, and visual signal if the transceiver is placed for optimal signal exchange between the analyte sensor and the transceiver.

In some embodiments, the interface device of the transceiver may receive analyte data from the analyte sensor, and the transceiver may comprise a processor configured to calculate an analyte concentration value based on the received analyte data. In some embodiments, the transceiver may include a wireless communication circuit configured to wirelessly transmit the analyte concentration to a smartphone or other device.

In some embodiments, the notification device may be configured to emit an aural alarm when the calculated analyte concentration value exceeds or falls below a threshold value. In some embodiments, the notification device may include a vibration motor configured to generate a vibrational signal when the calculated analyte concentration value exceeds or falls below a threshold value. In some embodiments, the notification device may include one or more LEDs configured to generate one or more visual signals.

In some embodiments, the transceiver may include a battery, and the notification device may be configured to generate one or more of a vibrational, aural, and visual signal if the power level of the battery falls below a threshold. In some embodiments, the transceiver may be an on-body, wearable transceiver.

Another aspect of the present invention may provide a system for detecting an amount or concentration of an analyte in vivo within a living organism. The system may include an analyte sensor and a transceiver. The analyte sensor may be configured to detect the analyte within the living organism. The analyte sensor may include indicator elements, sensor elements, and an interface device. The indicator elements may be configured to exhibit a detectable property based on the amount or concentration of the analyte in proximity to the indicator elements. The sensor elements may be configured to generate a data signal based on the detectable property exhibited by said indicator elements. The interface device may be configured to receive signals and generate power for powering the sensor elements and to convey data signals generated by the sensor elements. The transceiver may include an interface device and a notification device. The interface device may be configured to convey a power signal to the interface device of the analyte sensor and to receive data signals conveyed by the interface device of the analyte sensor. The notification device may be configured to generate one or more of a vibrational, aural, and visual signal based on a data signal received from the interface device of the analyte sensor.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF THE INVENTION

Figure 3:
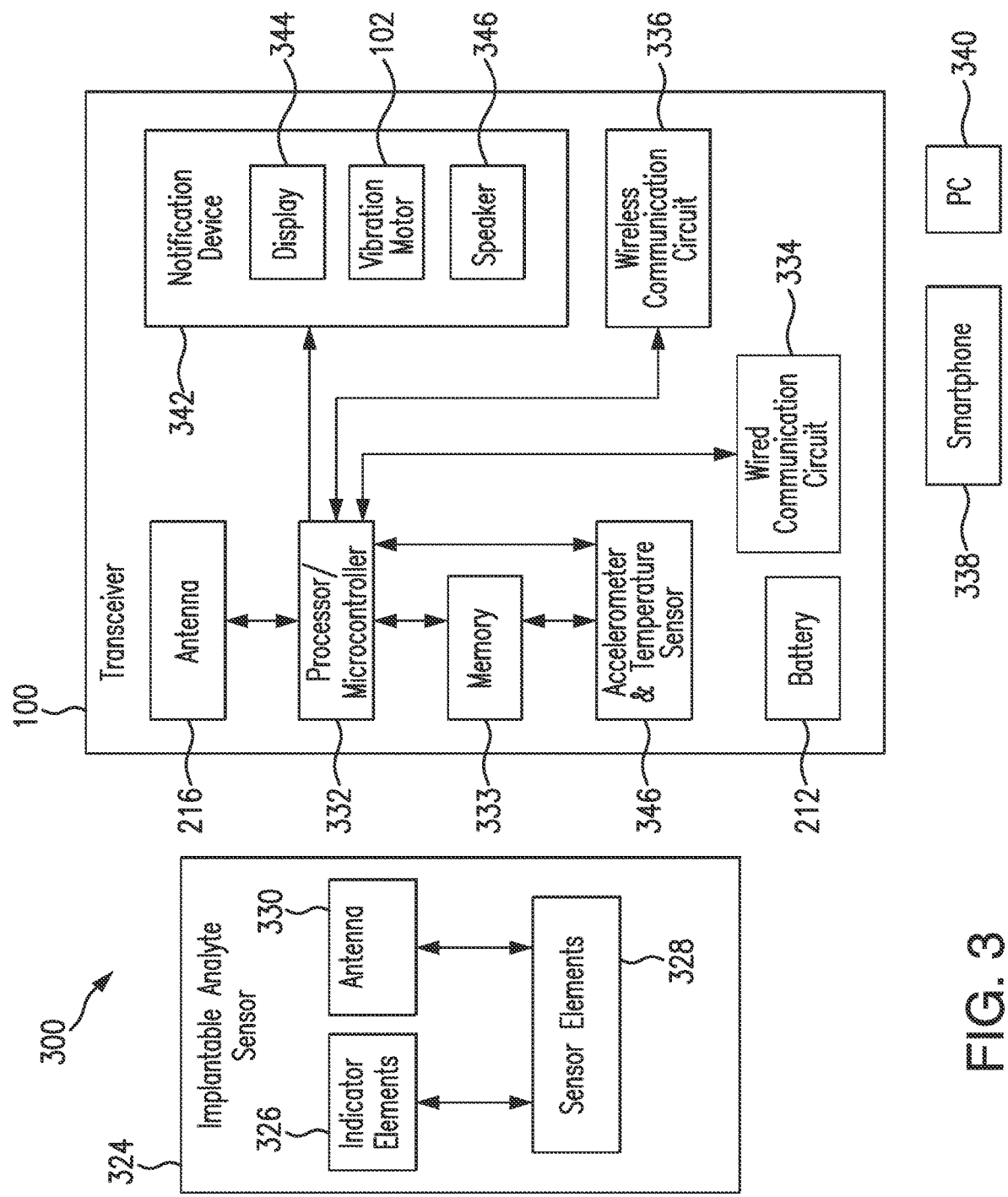
FIG. 3 is a schematic view of an analyte monitoring system embodying aspects of the invention.

FIG. 3 is a schematic view of an analyte monitoring system 300 embodying aspects of the present invention. The analyte monitoring system 300 may include a sensor 324 and an external transceiver 100 configured for communication with the sensor 324. In the embodiment shown in FIG. 3, the sensor 324 may be an implantable sensor configured to be implanted in a living animal (e.g., a living human). In some non-limiting embodiments, the sensor 324 may be an implantable sensor configured to be implanted, for example, in a living animal's arm, wrist, leg, abdomen, peritoneum, or other region of the living animal suitable for sensor implantation. For example, in one non-limiting embodiment, the sensor 324 may be implanted beneath the skin (e.g., in the subcutaneous tissues). In some embodiments, the sensor 324 may be an analyte sensor configured to detect an analyte (e.g., glucose or oxygen) in a patient's interstitial fluid, blood, or intraperitoneal fluid. In some embodiments, as illustrated in FIG. 3, the sensor 324 may include indicator elements 326 and sensor elements 328 to detect analyte data and convey/communicate the analyte data to the external transceiver 100.

In some embodiments, the transceiver 100 may be a handheld device or an on-body/wearable device. For example, in some embodiments where the transceiver 100 is an on-body/wearable device, the transceiver 100 may be held in place by a band (e.g., an armband, wristband, leg band, or belt) and/or adhesive, and the transceiver 100 may convey (e.g., periodically, such as every two minutes, and/or upon user initiation) measurement commands (i.e., requests for measurement information) to the sensor 324.

In some non-limiting embodiments, the transceiver 100 may receive analyte data from the sensor 324 and calculate an analyte concentration based on the received analyte data. In a non-limiting embodiment, the transceiver 100 may include a processor 332 that performs the analyte concentration calculation. In some non-limiting embodiments, the analyte concentration calculation may include one or more features described in U.S. Patent Application Publication No. 2014/0018644, which is incorporated by reference in its entirety. The transceiver 100 may also include memory 333 (e.g., Flash memory), which may be non-volatile and/or capable of being electronically erased and/or rewritten. The memory 333 may store analyte data received from the sensor 324 and/or calculated analyte concentrations.

In some embodiments, the sensor 324 may include an antenna 330, and the sensor 324 may wirelessly convey the analyte data to the external transceiver 100. The transceiver 100 may include an antenna 216 that is capable of coupling with the antenna 330 of the sensor 324. The antenna 216 may wirelessly receive analyte data and/or other data (e.g., temperature data) from the sensor 324 and/or may wirelessly convey power and/or data (e.g., commands) to the sensor 324. However, it is not required that the sensor 324 and transceiver 100 have antennas, and, in alternative embodiments, the system 300 may include a transdermal needle tip that provides a wired connection between the external transceiver 100 and the sensor 324. In these embodiments, the sensor 324 may convey the analyte data to the transceiver 100 via the wired connection provided by the transdermal needle tip, and the transceiver 100 may convey power and/or data (e.g., commands) to the sensor 324 via the wired connection provided by the transdermal needle tip.

In some embodiments, the transceiver 100 may have a wired communication circuit 334 that enables wired connection to an external device, such as a smartphone 338 or personal computer (PC) 340. In some non-limiting embodiments, the wired communication circuit 334 may include a connector, such as, for example, a Micro-Universal Serial Bus (USB) connector. However, in alternative embodiments, other connectors may be used. The transceiver 100 may exchange data to and from the external device through the wired communication circuit 334 and/or may receive power through the wired communication circuit 334.

In some embodiments, the transceiver 100 may wirelessly transmit the calculated analyte concentration to a smartphone 338 or other external device. In a non-limiting embodiment, the transceiver 100 may include a wireless communication circuit 336 to wirelessly transmit the analyte concentration. The wireless communication circuit 336 may employ one or more wireless communication standards to wirelessly transmit the data. The wireless communication standard(s) employed may include any suitable wireless communication standard, such as, for example, an ANT standard, a Bluetooth standard, or a Bluetooth Low Energy (BLE) standard (e.g., BLE 4.0).

Figure 1:
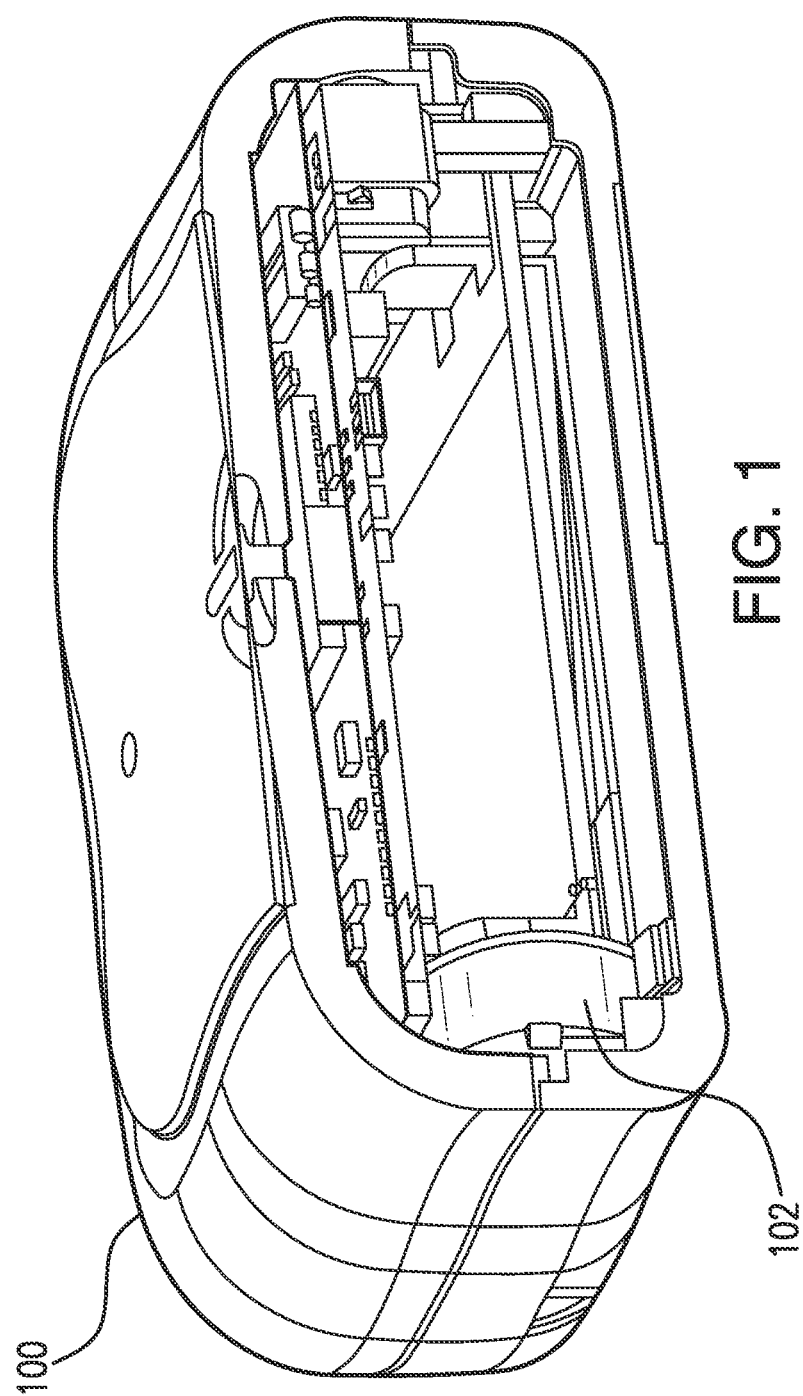
FIG. 1 is cross-sectional, perspective view of a transceiver embodying aspects of the invention.
Figure 2:
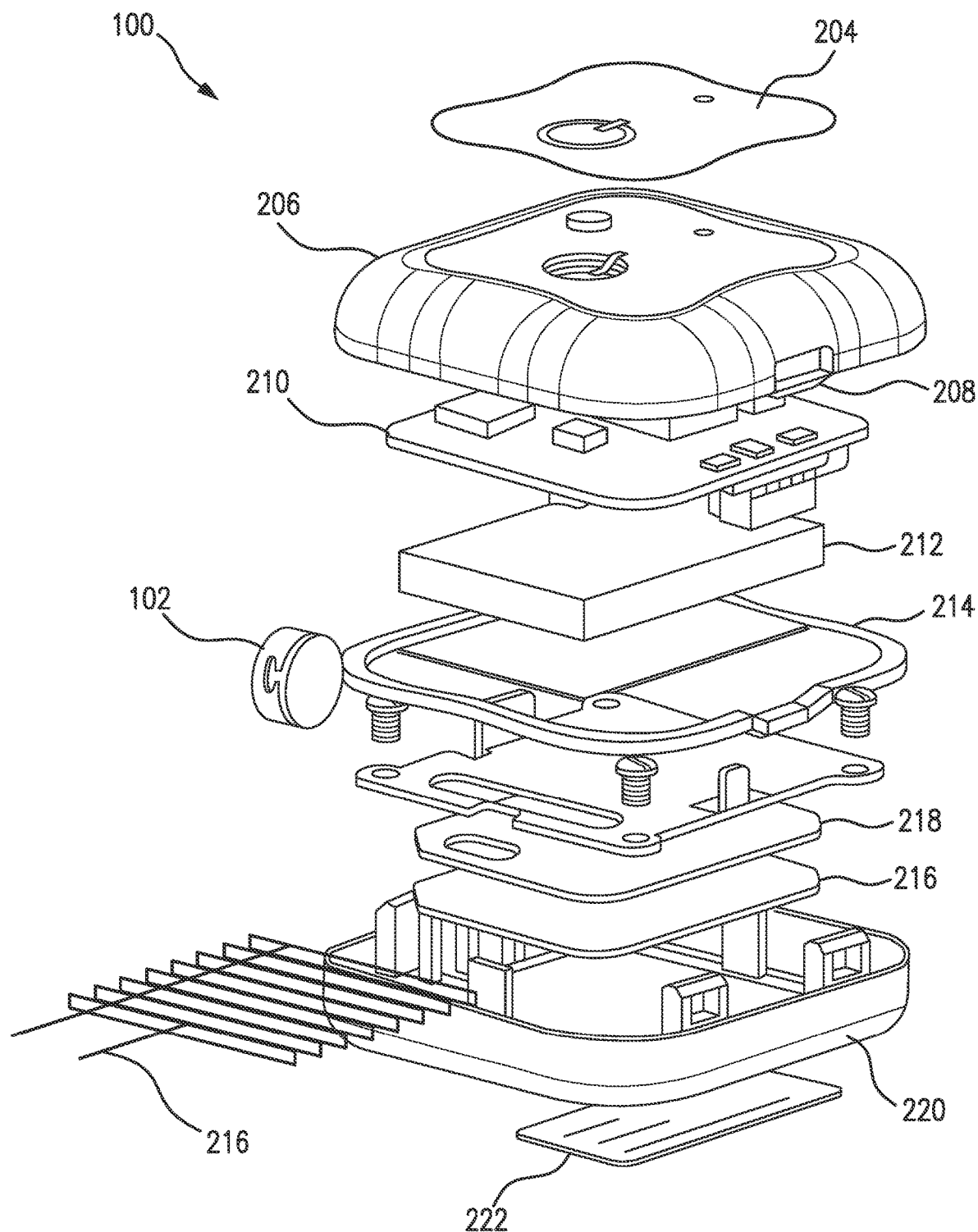
FIG. 2 is an exploded, perspective view of a transceiver embodying aspects of the invention.

FIGS. 1 and 2 are cross-sectional and exploded views, respectively, of a non-limiting embodiment of the transceiver 100, which may be included in the analyte monitoring system 300. As illustrated in FIG. 2, in some non-limiting embodiments, the transceiver 100 may include a graphic overlay 204, front housing 206, button 208, printed circuit board (PCB) assembly 210, battery 212, gaskets 214, antenna 216, frame 218, back housing 220, ID label 222, and/or vibration motor 102. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. However, this is not required, and in some alternative embodiments, the front housing 206 and back housing 220 in another manner (e.g., ultrasonic welding). In some embodiments, the full assembly process may be performed at a single external electronics house. However, this is not required, and, in alternative embodiments, the transceiver 100 may be performed at one or more electronics houses, which may be internal, external, or a combination thereof. In some embodiments, the assembled transceiver may be programmed and functionally tested. In some embodiments, assembled transceivers 100 may be packaged into their final shipping containers and be ready for sale.

In some embodiments, the transceiver 100 may provide on-body alerts to the user in a visual, aural, and/or vibratory manner, regardless of proximity to a smartphone. In some non-limiting embodiments, as illustrated in FIG. 3, the transceiver 100 may include a notification device 342 that generates visual, aural, and/or vibratory alerts. In one non-limiting embodiment, the notification device 342 may include one or more of a display 344, a vibration motor 102, and a speaker 346, which respectively generate the visual, aural, and/or vibratory alerts. In some embodiments, the transceiver 100 may be configured to vibrate and/or generate an audio or visual signal to prompt the user about analyte readings outside an acceptable limit, such as hypo/hyper glycemic alerts and alarms in the case where the analyte is glucose.

In some embodiments, the vibrational, visual, and/or aural tone feedback provided by the transceiver 100 can enable the use of different patterns/rhythms/melodies that have various meanings corresponding to the status of the transceiver 100 or the inserted sensor 324, or the analyte concentration. For example, in one non-limiting embodiment, the transceiver 100 might be calibrated to provide a long, repeatable vibration, with or without an aural or visual alarm, when a user's glucose concentration becomes too low or too high. In some embodiments, a vibration motor 102 of the transceiver 100 may communicate various messages/alerts to the user through Morse code like patterning and sequencing (e.g., long-long-short-short) and/or different vibration speeds and intensities. In a non-limiting embodiment, a circuit, such a supply voltage controller, may control the vibration speed and intensity. In some embodiments, different patterns of audio feedback, which may include different volumes, frequencies, time on-off (duty cycle), melodies, and/or rhythms may be used to communicate various messages/alerts to the user. The vibration motor could also be set via an interface to wake up the subject with various vibration patterns.

In some embodiments, the display 344 may be any suitable display such as, for example and without limitation, a display that includes one or more light emitting diodes (LEDs), one or more liquid crystal displays (LCDs), and/or one or more organic light emitting devices (OLEDs). In some non-limiting embodiments, the transceiver 100 might be calibrated to provide a visual alert (e.g., one or more LEDs or other light sources may turn on and off in a specific pattern and/or emit light of different intensities and/or frequencies/colors) when a user's glucose concentration becomes too low or too high. For example, in some non-limiting embodiments, the display 344 of the notification device 342 may be capable of displaying more than one color. For instance, in some non-limiting embodiments, the display 344 may include dual LED (e.g., yellow/green) or a tri-color LED (i.e., blue/yellow/green). A display 344 providing different colors may enhance communication modes by adding color as variable. For instance, by using more than one LED (e.g., the dual LED or the tri-color LED) or other light source, the display 344 may generate a blinking yellow-green-yellow-etc. visual signal and/or a long yellow-short yellow-short green-short green-etc. visual signal to communicate various messages/alerts to the user.

In a non-limiting embodiment, the combination of visual, aural, and/or vibratory patterns may communicate different messages/alerts than if the visual, aural, and/or vibratory patterns were communicated alone. In some embodiments, the transceiver 100 may provide certain patterns of a vibratory and/or aural and/or visual alert to prompt the user when a calibration point is needed or is going to be needed, and/or when the battery (e.g., battery 212) has low power (e.g., a power level below a threshold) and needs to be recharged. In some embodiments, the smartphone 338 or other device communicating with the transceiver may also have visual, aural, or vibratory alarms and notifications.

The vibrational, visual, and/or aural feedback of the transceiver 100 can also alert the user regarding the status of the telemetry system with the sensor 324. For example, for systems in which transceiver 100 delivers power to the sensor 324 (e.g., by radio frequency signals via an inductive antenna), the visual, aural, and/or vibratory feedback can prompt the subject regarding how well the two systems are coupled. In other embodiments, the vibrational and/or aural feedback of the transceiver 100 can assist the user in adjusting the relative position of the transceiver 100 and optimize coupling between the transceiver 100 and the sensor 324 without having visual feedback. That is, the user can adjust the position of the transceiver 100 worn under a piece of clothing (e.g., shirt, etc.) without looking at the transceiver 100—the buzzer/vibrator signals of the transceiver 100 would indicate to the user if the sensor 324 is well within the range and if the readings are correct. Accordingly, in some embodiments, the transceiver 100 may be used to alert the user to an optimal location of the transceiver 100 over the implanted sensor (e.g., a location in which the transceiver 100 and sensor 324 are inductively coupled), which allows the user to adjust the transceiver 100.

Embodiments of the present invention also include novel ways for building in the vibration motor 102 to the transceiver PCB assembly 210 and housing 206 and 220. The assembly of the vibration motor 102 in the housing enables the coupling of force to the subject. In some embodiments, the axis of vibration may be perpendicular with the body contacting surface of the transceiver 100 to efficiently couple the force of the vibration to the subject. However, this is not required, and, in some alternative embodiments, the axis of vibration may be co-planar with the body contact surface. In some embodiments, the vibration motor 102 may be attached to the transceiver housing, frame, or other components within the transceiver 100. In some embodiments, attachment of the vibration motor 102 to the transceiver housing enables an aural alert out of the vibration motor 102, by creating an audible sound as the vibration motor 102 vibrates against the internal surface of the transceiver 100. The vibration motor 102 may be attached to a special membrane, which may amplify the audio aspect of the vibration and act as a speaker cone membrane. In other embodiments, the vibrational and/or aural feedback of the transceiver 100 can be combined with a variable vibration speed system by controlling the supply voltage to vibration motor 102. This would enable both tactile/audio feedback intensity to be varied and enhance communication modes.

In some embodiments, the transceiver 100 may include an accelerometer and temperature sensor unit 346. The accelerometer and temperature sensor unit 346 may include an accelerometer that monitors motion. In some non-limiting embodiments, the accelerometer may improve analyte monitoring by providing motion information that can be used to help determine movement-related artifacts or noise that may be present within the monitoring signal. In other embodiments, the transceiver 100 may additionally or alternatively use information from the accelerometer to provide feedback to the user of the device in order to aid the user in, for example, moving the sensor 324 to the correct position or orientation. In other embodiments, the accelerometer may be used for sleep monitoring. In some non-limiting embodiments, the analyte monitoring system may include different analyte pattern recognition parameters (e.g., different glycemic pattern recognition parameters) for different states, such as, for example, awake/active, awake/sedentary, and/or asleep. This further information may be translated into different alarm types for the subject. Furthermore, the transceiver 100 may have a settable alarm clock functionality, and the transceiver 100 may alert the user following sleep pattern and activity levels.

In some embodiments, the accelerometer may act as a button like interface. This would alleviate the need to have a mechanical button, or the button like interface of the accelerometer could be used in addition to one or more mechanical buttons.

In some embodiments, the transceiver 100 may notify a smartphone (e.g., smartphone 338) of an emergency condition. In some non-limiting embodiments, the transceiver 100 may detect an emergency condition if the accelerometer detects a period of low acceleration followed by high acceleration (e.g., a fall event). In some non-limiting embodiments, the transceiver 100 may detect an emergency condition if alarms are ignored (e.g., no receipt of user input) for a period of sustained hypoglycemia or hyperglycemia. In some embodiments, notifying the smartphone of an emergency condition may cause the cause the smartphone to contact (e.g., via email or text) one or more emergency contacts. In this manner, the transceiver 100 may enable automatic emergency contact for emergency conditions such as, for example, hypoglycemic shock.

The transceiver 100 may include functionality to act as the hub for body worn or local proximity sensors. These sensors could include, for example, oxygen levels or pulse oximeters, sweat detectors, heart rate monitors, and/or gyroscopes. Inclusion of one or more temperature sensors enable the ability to track core, subcutaneous and skin temperature, which could provide feedback on physiological states as well. These body worn or local proximity sensors could communicate using a wireless communication standard (e.g., BLE) or be directly wired to the transceiver 100. The transceiver 100 may log data received from the body worn or local proximity sensors and transmit the data (e.g., using a wireless communication standard) to a paired smartphone 338 or PC 340, cellular or Wi-Fi. In some embodiments, the transceiver 100 may have a direct interface to an insulin pump to control dosing of bolus or basal rates depending on glycemic or other measurements. In some non-limiting embodiments, the sensor hub may provide an interface for feedback of body movements and physiological signals (e.g., for use with a gaming system that interacts with movements of the human body).

In some embodiments, the transceiver 100 may have various forms of energy harvesting mechanisms to slowly charge the battery 212 in order to increase uninterrupted run time. For example, in one non-limiting embodiment, the transceiver 100 may include a solar panel on the transceiver enclosure (e.g., on front housing 206). For another example, the transceiver 100 may additionally or alternatively include one or more of thermo-, magneto-, piezo-, vibration, and/or movement mechanisms, etc. as a source of energy. In one non-limiting embodiment, the electromagnetic waves from cellular telephony, Bluetooth, GPS, Wi-Fi, or other frequency bands can be used for harvesting energy.

In some embodiments, the transceiver 100 may include splash-proof or waterproof features. This would enable the user to use the transceiver 100 according to appropriate splash-proof or waterproof guidelines. For example, in embodiments where the transceiver 100 is waterproof, a user could take as shower while wearing the waterproof transceiver 100.

In some embodiments, the transceiver 100 may include a secondary processor. In some embodiments, the secondary processor may be part of the wireless communication circuit 336 and may perform the functionality of communicating according to a wireless communication standard (e.g., BLE). In embodiments where the transceiver 100 includes a secondary processor, the secondary processor may help processor 332 handle some peripherals. For example, the secondary processor may help to handle interrupts from buttons, drive LEDs (e.g., in display 344), control vibration motor 102, buzzer or speaker 346, etc. This way transceiver 100 could potentially save energy by using the secondary processor instead of processor 332. Use of the secondary processor may also enable use of a smaller package for processor 332 with less pins. The secondary processor and processor 332 may be connected through an I/O internal interface exchanging data and commands. The secondary processor and processor 332 may wake up each other and perform certain tasks. This way, one or both of the secondary processor and processor 332 may "sleep" until activity is needed. In some embodiments, the secondary processor (e.g., when part of the wireless communication circuit) may be used to upgrade the firmware of processor 332 wirelessly so no wired/physical connection would be needed.

In some embodiments, the transceiver 100 may incorporate a headset (e.g., a BLE headset). In some non-limiting embodiments, the headset may be suitable for blind and/or visually impaired people. The headset may inform the user about analyte levels, alerts, coupling issues, reminders, etc. The headset may have microphone so the user can issue voice command to a smartphone 338 and/or transceiver 100. In some non-limiting embodiments, using the headset, the user may be able to issue voice commands such as, for example, measure analyte now, battery level, tell me the glucose trend, time, etc. The headset may use the wireless communication circuit 336 of the transceiver 100 (e.g., internal transceiver BLE) for issuing voice commands, or the headset may request and use iPod/iPhone/smartphone/etc. for that purpose. However, in some alternative embodiments, the transceiver 100 may have an internal microphone and speaker so that a headset would not be needed, and the transceiver 100 may instead perform the functionally of the headset described above.

In some embodiments, the transceiver 100 may have a display 344. The display 344 may provide information about one or more of, for example, time, date, analyte values, trends, activities log, alerts/alarms, battery level, sensor signal, BLE signal, etc. In some non-limiting embodiments, the display 344 may be a color display and/or may be a high resolution display or an organic light emitting device (OLED) display. In some embodiments, all useful information (or at least vital information) may be available through the display 344 so that the patient does not have to rely on a smartphone (e.g., smartphone 338).

In some non-limiting embodiments, the transceiver 100 may have embedded (web) radio, video, and mp3 player capabilities. In some non-limiting embodiments, the display 344 may enable WWW, chat, social games, and services like competing with fellow users in calories/steps counts, etc. For example, the WWW capability may be achieved by using Wi-Fi enabled ICs.

In some embodiments, the transceiver 100 may have a battery 212. In some non-limiting embodiments, the battery 212 may be a disposable or rechargeable battery. In some non-limiting embodiments, the battery 212 may be a replaceable battery. With the ability to swap replaceable batteries, one transceiver 100 could be used with a plurality of swappable batteries for longer periods between charging, which would be useful during times when recharging is not possible (e.g., camping, traveling, etc.). In some non-limiting embodiments, transceiver 100 may be compatible with bigger, swappable batteries so the user could use transceiver 100 for longer time while accepting increased transceiver size.

In some embodiments, the accelerometer and temperature sensor unit 346 may include a temperature sensor (e.g., a thermistor, thermocouple, or resistance temperature detector). The temperature sensor may be used monitor body temperature. In some non-limiting embodiments, as illustrated in FIG. 3, the accelerometer and temperature sensor may be part of a single unit 346. However, this is not required, and, in some alternative embodiments, the accelerometer and temperature sensor may be provided as separate units, or the transceiver 100 may include only one of the accelerometer and the temperature sensor.

In some embodiments, the transceiver 100 may include a Global Positioning System (GPS) unit having the functionality to acquire a GPS signal. The GPS unit may implement hardware and/or software functionality that enables monitoring of motion. In some non-limiting embodiments, the GPS unit may improve glucose monitoring by providing motion information that can be used to help determine movement-related artifacts or noise that may be present within the monitoring signal. In some embodiments, the GPS unit may provide the transceiver 100 with the ability to communicate exact positions for patients that may go into hypoglycemic shock and would need emergency personal notified of their location for treatment. For example, the location of the patient may be communicated through the transceiver's wireless capabilities and/or through a cellular or Wi-Fi handset.

In some embodiments, the transceiver 100 may include an ambient light sensor (e.g., photodiodes, phototransistors, photoresistors or other photosensitive elements). In some non-limiting embodiments, the ambient light sensor may be used to predict potential ambient light issues. For instance, in embodiments where the sensor 324 is an optical sensor, ambient light could interfere with the sensor's analyte measurements, the ambient light sensor could be used to flag or indicate analyte measurements that may not be reliable due to ambient light (e.g., when ambient light exceeds one or more thresholds). In other embodiments, transceiver 100 may incorporate the measured intensity of ambient light into the calculation of analyte concentration.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, circuitry of the sensor and transceiver may be implemented in hardware, software, or a combination of hardware and software. The software may be implemented as computer executable instructions that, when executed by a processor, cause the processor to perform one or more functions. For another example, although the vibration motor 102 is illustrated in FIGS. 1 and 2 as having a cylindrical shape, this is not required, and, in alternative embodiments, vibration motors having other shapes may be used.

What is claimed is:

1. A system comprising:
   an analyte sensor configured to detect an analyte within a living animal;
   an accelerometer configured to generate motion information; and
   a transceiver including:
      an interface device configured to receive data signals conveyed by the analyte sensor;
      a notification device; and
      a processor configured to:
         calculate an analyte concentration value based on one or more of the data signals conveyed by the analyte sensor;
         use the motion information to determine a state of the living animal;
         use the determined state of the living animal to select among different analyte pattern recognition parameters for different states;
         use the calculated analyte concentration value to determine whether the selected analyte pattern recognition parameter is met; and
         control the notification device to generate a notification signal if the selected analyte pattern recognition parameter is met.

2. The system of claim 1, wherein the analyte sensor comprises:
   indicator elements configured to exhibit a detectable property based on an amount or a concentration of the analyte in proximity to the indicator elements;
   sensor elements configured to generate the data signals based on the detectable property exhibited by said indicator elements; and
   an interface device configured to convey the data signals generated by said sensor elements.

3. The system of claim 2, wherein the interface device of the analyte sensor is an antenna configured to wirelessly convey the data signals generated by said sensor elements, and the interface device of the transceiver is an antenna configured to receive the data signals from the antenna of the analyte sensor.

4. The system of claim 2, wherein the interface devices of the transceiver and the analyte sensor are a wired connection through a transdermal needle tip.

5. The system of claim 1, wherein the interface device of the transceiver comprises an antenna capable of coupling with an antenna of the analyte sensor, and the processor is further configured to control the notification device to generate a second notification signal indicative of the coupling between the antennas of the analyte sensor and the transceiver.

6. The system of claim 1, wherein the processor is further configured to control the notification device to generate a second notification signal if the power level of a battery of the transceiver falls below a threshold.

7. The system claim 1, wherein the analyte sensor is an implantable analyte sensor.

8. The system of claim 1, wherein the transceiver further comprises a communication circuit configured to transmit data to an external device.

9. The system of claim 8, wherein the external device is configured to generate a vibrational signal.

10. The system of claim 1, wherein the interface device comprises a wired connection to the analyte sensor through a transdermal needle tip.

11. The system of claim 1, wherein the different states include active, sedentary, and asleep.

12. The system of claim 1, wherein the processor is further configured to detect an emergency condition if the accelerometer detects a period of low acceleration followed by high acceleration.

13. The system of claim 12, wherein the processor is further configured to use a communication circuit of the transceiver to notify an external device of the emergency condition.

14. The system of claim 1, wherein the transceiver comprises the accelerometer.

15. The system of claim 1, further comprising adhesive configured to hold the transceiver in place on the body of the living animal.

16. The system of claim 1, wherein the notification device comprises a vibration motor.

17. A method comprising:
using an analyte sensor to detect an analyte within a living animal;
using an accelerometer to generate motion information;
using an interface device of a transceiver to receive data signals conveyed by the analyte sensor;
using a processor of the transceiver to calculate an analyte concentration value based on one or more of the data signals conveyed by the analyte sensor;
using the processor of the transceiver to determine a state of the living animal based on the motion information;
using the processor of the transceiver to select among different analyte pattern recognition parameters for different states based on the determined state of the living animal;
using the processor of the transceiver to determine that the selected analyte pattern recognition parameter is met based on the calculated analyte concentration value; and
using the processor of the transceiver to control a notification device to generate a notification signal if the selected analyte pattern recognition parameter is determined to be met.

18. The method of claim 17, wherein the different states include active, sedentary, and asleep.

19. The method of claim 17, further comprising:
using the accelerometer to detect a period of low acceleration followed by high acceleration; and
using the processor of the transceiver to detect an emergency condition if the accelerometer detects the period of low acceleration followed by high acceleration.

20. The method of claim 19, further comprising using the processor of the transceiver to use a communication circuit of the transceiver to notify an external device of the emergency condition.

21. The system of claim 1, wherein the notification signal is one or more of a vibrational, aural, and visual signal.

22. The system of claim 5, wherein the second notification signal is one or more of a vibrational, aural, and visual signal.

23. The system of claim 6, wherein the second notification signal is one or more of a vibrational, aural, and visual signal.

24. The method of claim 17, wherein the notification signal is one or more of a vibrational, aural, and visual signal.

* * * * *